United States Patent
Ben-Asouli et al.

(10) Patent No.: US 8,241,477 B2
(45) Date of Patent: Aug. 14, 2012

(54) DOUBLE CHAMBER TANK FOR HORIZONTAL GEL ELECTROPHORESIS

(75) Inventors: Yitzhak Ben-Asouli, Kfar Hanagid (IL); Farhat Osman, Sachnin (IL)

(73) Assignee: Gene Bio-Application Ltd., Kfar Hanagid (IL)

( * ) Notice: Subject to any disclaimer, the term of this patent is extended or adjusted under 35 U.S.C. 154(b) by 483 days.

(21) Appl. No.: 11/815,396

(22) PCT Filed: Jan. 16, 2006

(86) PCT No.: PCT/IL2006/000060
§ 371 (c)(1), (2), (4) Date: Sep. 27, 2007

(87) PCT Pub. No.: WO2006/082575
PCT Pub. Date: Aug. 10, 2006

(65) Prior Publication Data
US 2008/0217178 A1   Sep. 11, 2008

(30) Foreign Application Priority Data
Feb. 7, 2005 (IL) ......................... 166716

(51) Int. Cl.
*G01N 27/453* (2006.01)
(52) U.S. Cl. ........ 204/616; 204/450; 204/456; 204/466; 204/606
(58) Field of Classification Search ................ 204/403.01–403.15, 450, 456, 466, 606, 204/615, 616, 621; 205/777.5, 778, 792; 600/345–348; 435/4–40.52; 436/516
See application file for complete search history.

(56) References Cited

U.S. PATENT DOCUMENTS

| | | | | |
|---|---|---|---|---|
| 3,873,433 A * | 3/1975 | Seidel et al. | | 204/462 |
| 4,588,491 A | 5/1986 | Kreisher et al. | | |
| 5,779,869 A | 7/1998 | Helfer et al. | | |
| 6,063,250 A * | 5/2000 | Becker | | 204/450 |
| 6,212,705 B1 * | 4/2001 | Kramer | | 4/559 |
| 2001/0037940 A1 * | 11/2001 | Shih et al. | | 204/466 |
| 2004/0020775 A1 * | 2/2004 | Ben-Asouli et al. | | 204/615 |
| 2004/0050699 A1 * | 3/2004 | Goncalves | | 204/450 |

FOREIGN PATENT DOCUMENTS

| | | | |
|---|---|---|---|
| DE | 227742 A1 * | 9/1985 | |
| WO | WO 01/55707 A | 8/2001 | |
| WO | WO 02/37094 A | 5/2002 | |

OTHER PUBLICATIONS

Machine translation of abstract for DD227742A1, Sep. 1985.* International Search Report for PCT/IL06/00060.
International Preliminary Report on Patentability for PCT/IL06/00060.

* cited by examiner

*Primary Examiner* — Kaj K Olsen
*Assistant Examiner* — Susan D Leong
(74) *Attorney, Agent, or Firm* — Martin Felit; Paul D. Bianco; Fleit Gibbons Gutman Bongini & Bianco PL

(57) ABSTRACT

A tank apparatus (10) for horizontal electrophoresis that comprises a base member (12) having at least first and second independent receptacles (16, 18) for accommodating buffer solution. Each of the receptacles comprises an inlet (28, 28') for allowing communication with the external environment. A cover member (14) covers at least the first and second receptacles, thereby forming first and second buffer chambers. The cover member comprising suitable openings (40, 42) for allowing a portion of an electrophoresis gel cassette to be inserted therethrough, such that the electrophoresis gel is in communication with the contents of each of the first and second receptacles. Each of a pair of electrodes (33, 33') is situated in one of each of the first and second receptacles, wherein the electrodes are connectable to an electrical power supply.

15 Claims, 15 Drawing Sheets

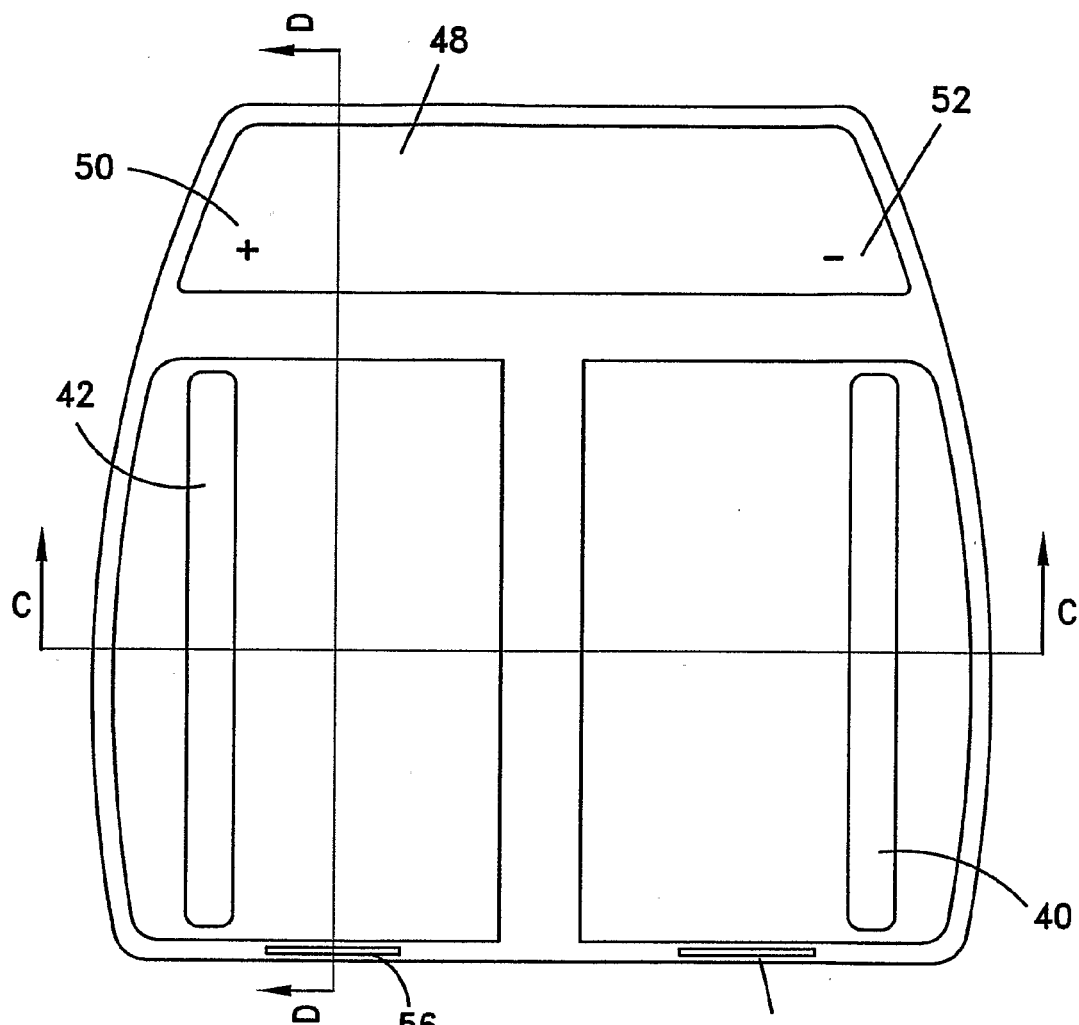
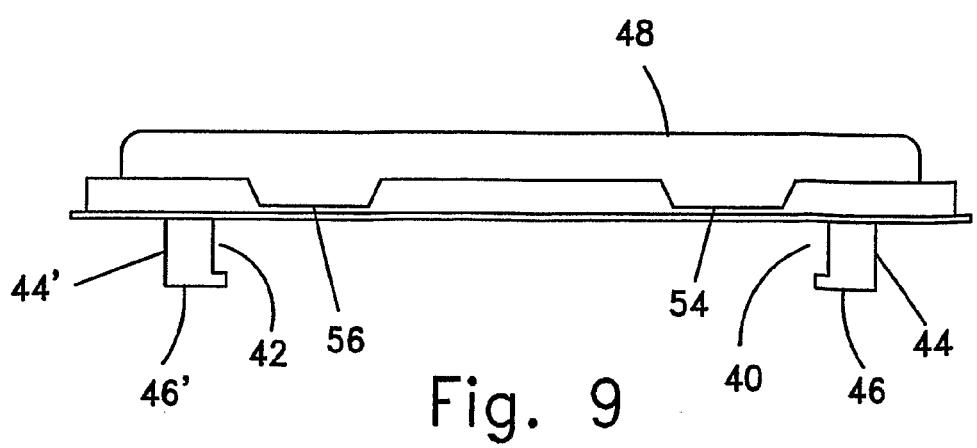
Fig. 8
Fig. 9

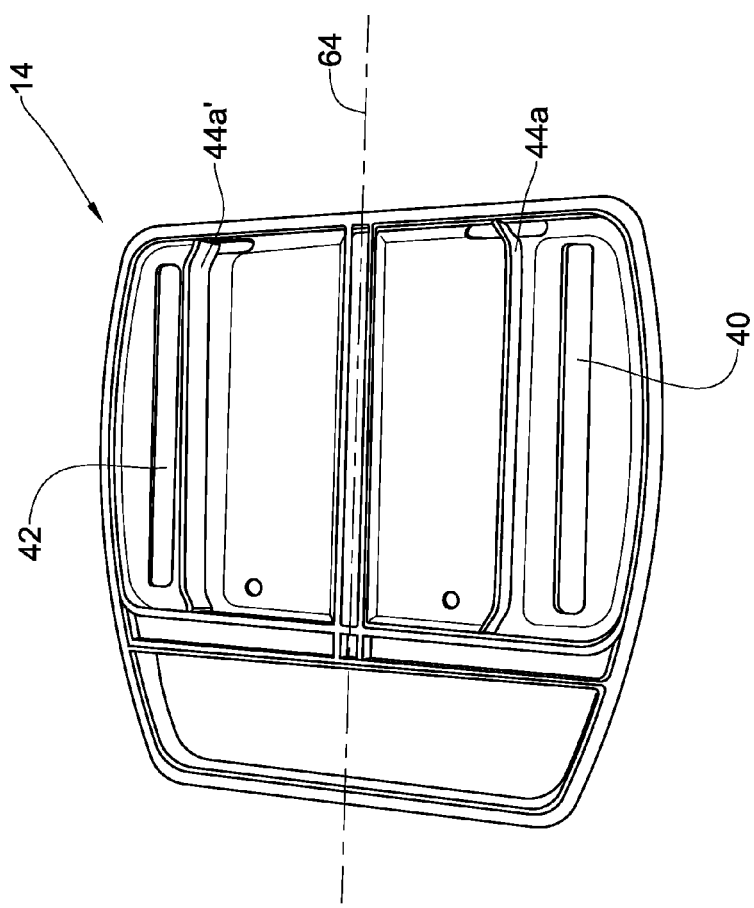

DOUBLE CHAMBER TANK FOR HORIZONTAL GEL ELECTROPHORESIS

TECHNICAL FIELD

The present invention relates generally to a tank for accommodating a buffer solution, and which is used for semi dry electrophoresis. Particularly, the present invention relates to a tank apparatus which comprises two independent buffer chambers that are not in communication with one another, however, each chamber is in mutual communication with a gel matrix.

BACKGROUND

Electrophoresis is an analytical technique for separating and identifying charged particles, ions, or molecules. Electrophoresis involves the imposition of an electric field in order to move a charged species in a medium. The molecules to be separated are placed in wells of a gel medium which comes in contact with a buffer contained in a tank. The most often studied species are bio-macromolecules, such as proteins and nucleic acids (e.g. RNA molecules and DNA fragments), which are usually polyelectrolytes. However, electrophoresis can be used to separate any charged materials including various cells, bacteria and viral materials.

At a fixed pH and ionic strength, a given polyelectrolyte acquires a certain number of net charges. Such particles are surrounded by counter-ions and have various charges and sizes (volume and shape) which affect movement.

Molecules are differentiated by their different mobility's under an applied electric field. The mobility variation derives from the different charge and frictional resistance characteristics of the molecules. The more charged and streamlined the molecules, the faster their movement. The positively charged molecules will move to the negative electrode (cathode) and the negatively charged molecules will move to the positive electrode (anode).

When a mixture containing several molecular species is introduced to an electrophoretic separation medium and an electric field is applied, the different charged components migrate at varying speeds, producing the resolution of the mixture. The location of each of the separated bands depends on the mobility of each component, on the interaction of the polyelectrolytes with the surrounding medium via the influence of pH, ionic strength, ion type and on whether the medium is a buffered solution of ions, polymeric solution, or gel such as a cross-linked gel. The most frequently used gel media are based on polyacrylamide (known as PAGE) and agarose gels.

Vertical electrophoresis apparatuses use acrylamide gels for the separation of proteins and small nucleic acid molecules. These systems include a set of vertically disposed glass plates within which the gel is held and an upper and a lower buffer chamber. The use of two separated vertical buffer chambers presents a number of inconveniences. For instance, the buffer volume needed to fill both chambers is usually large. Additionally, during the vertical electrophoresis process, the upper chamber often leaks. If the upper chamber is not refilled quickly, the results may be distorted and valuable samples could be lost. Moreover, uniform heat distribution across the gel is necessary for even banding separation and reproducibility. However, the use of two vertical isolated buffer chambers may result in a non-uniform heat distribution across the gel.

Prior art horizontal electrophoresis apparatuses are designed for easy separation of large nucleic acid molecules on agarose gels. These apparatuses, however, require a large volume of buffer in order to completely submerge the gel.

It is an object of the present invention to benefit from the advantages of both the vertical and horizontal gel apparatuses. The electrophoretic tank of the present invention is designed for horizontal gel electrophoresis, utilizing both agarose gel for nucleic acid electrophoresis and polyacrylamide gel for small nucleic acid molecules and protein electrophoresis.

A further object of the present invention is to provide an electrophoresis gel tank that is portable, and is easy and safe to use.

The electrophoresis device disclosed in the invention may be particularly used with a gel device as described in WO 02/37094, which describes a gel device that overcomes the inconveniences involved with vertical electrophoresis. The gel device comprises a gel cassette with two open legs to allow ionic communication with the buffer in the chambers. The gel cassette may include an agarose gel, a polyacrylamide gel, a gradient gel or a hybrid agarose-polyacrylamide gel precasted.

SUMMARY

The present invention relates to a tank apparatus for horizontal electrophoresis comprising:
  a. a base member comprising at least first and second independent receptacles for accommodating buffer solution, wherein each of said receptacles comprises an inlet for allowing communication with the external environment;
  b. a cover member for covering at least said first and second chambers, said cover member comprising suitable openings for allowing a portion of an electrophoresis gel cassette to be inserted therethrough, such that said electrophoresis gel is in communication with the contents of each of said first and second receptacles; and,
  c. a pair of electrodes, wherein each of said electrodes is situated in one of each of said first and second receptacles, and wherein said electrodes are connectable to an electrical power supply.

The receptacles are separated from one another by a first partition wall. Each of said receptacles comprises suitable supports for supporting each of said electrodes.

The supports consist of an array of pins that protrude vertically from the bottom of each of said receptacles, wherein the top of each of said pins contains a slit for accommodating said electrode. The power source is connected to the electrodes via electrically conductive wires.

The tank apparatus further comprises a third compartment, wherein said third compartment is in communication with each of said receptacles via said inlets, and wherein each of said electrodes is inserted into each of said receptacles through each of said inlets from said third compartment. Said third compartment is in further communication with an electrical power source. The power source is connected to the electrodes by electrically conductive wires.

The cover member of the tank apparatus further covers said third compartment, and comprises two suitable openings for accommodating an electrophoresis gel cassette. When the cover member is positioned above the receptacles, each of said suitable openings is aligned above one of said respective receptacles. The cover member contains at least one aperture which serves as a vent, located above each of said receptacles.

According to a preferred embodiment, a microswitch is situated in the third compartment. An outer casing, comprising a magnet, is situated on said outer casing such that when said outer casing is positioned above or below said apparatus, an electrical circuit is completed. The outer casing further comprises vent openings for allowing hot hair to exit said casing, and cool air to enter said casing.

Preferably, the cover comprises a heat sink situated at its upper surface.

The cover preferably comprises a leg extending downward from its underside for preventing gas bubbles produced in the buffer solution from reaching the said slots. Each leg is situated between one of each of said slots and the central longitudinal axis of the cover.

The tank apparatus preferably further comprising a low-power external power supply. A transformer is provided for converting the power supply from low power to high power.

The present invention is further directed to a method of conducting gel electrophoresis of a biological sample comprising the steps of:

a. providing a tank apparatus for horizontal electrophoresis comprising:
   i. a base member comprising at least first and second independent receptacles for accommodating buffer solution, wherein each of said receptacles has an inlet for allowing communication with the external environment;
   ii. a cover member for covering at least said first and second receptacles, thereby forming first and second buffer chambers, said cover comprising suitable openings for allowing a portion of an electrophoresis gel cassette to be inserted therethrough, such that said electrophoresis gel is in communication with the contents of each of said first and second receptacles; and,
   iii. a pair of electrodes, wherein each of said electrodes is situated in one of each of said first and second receptacles, and wherein said electrodes are connectable to an electrical power supply;
b. filling each of said receptacles with a suitable buffer solution;
c. providing a solidified gel matrix with wells within a gel electrophoresis cassette adapted to be accommodated on said cover member;
d. loading said sample into said gel well; and
e. connecting said electrodes to said electrical source via electrically conductive wires, thereby providing a suitable electric potential to said receptacles to activate the electrophoresis process.

BRIEF DESCRIPTION OF THE FIGURES

FIG. 8 illustrates a top view of the cover of the apparatus of the present invention.

FIG. 9 illustrates a front view of the cover of the apparatus of the present invention.

FIG. 10a illustrates an alternative arrangement of the legs the extend from the underside of the cover of the apparatus of the present invention.

DETAILED DESCRIPTION OF PREFERRED EMBODIMENTS

Figure 1:
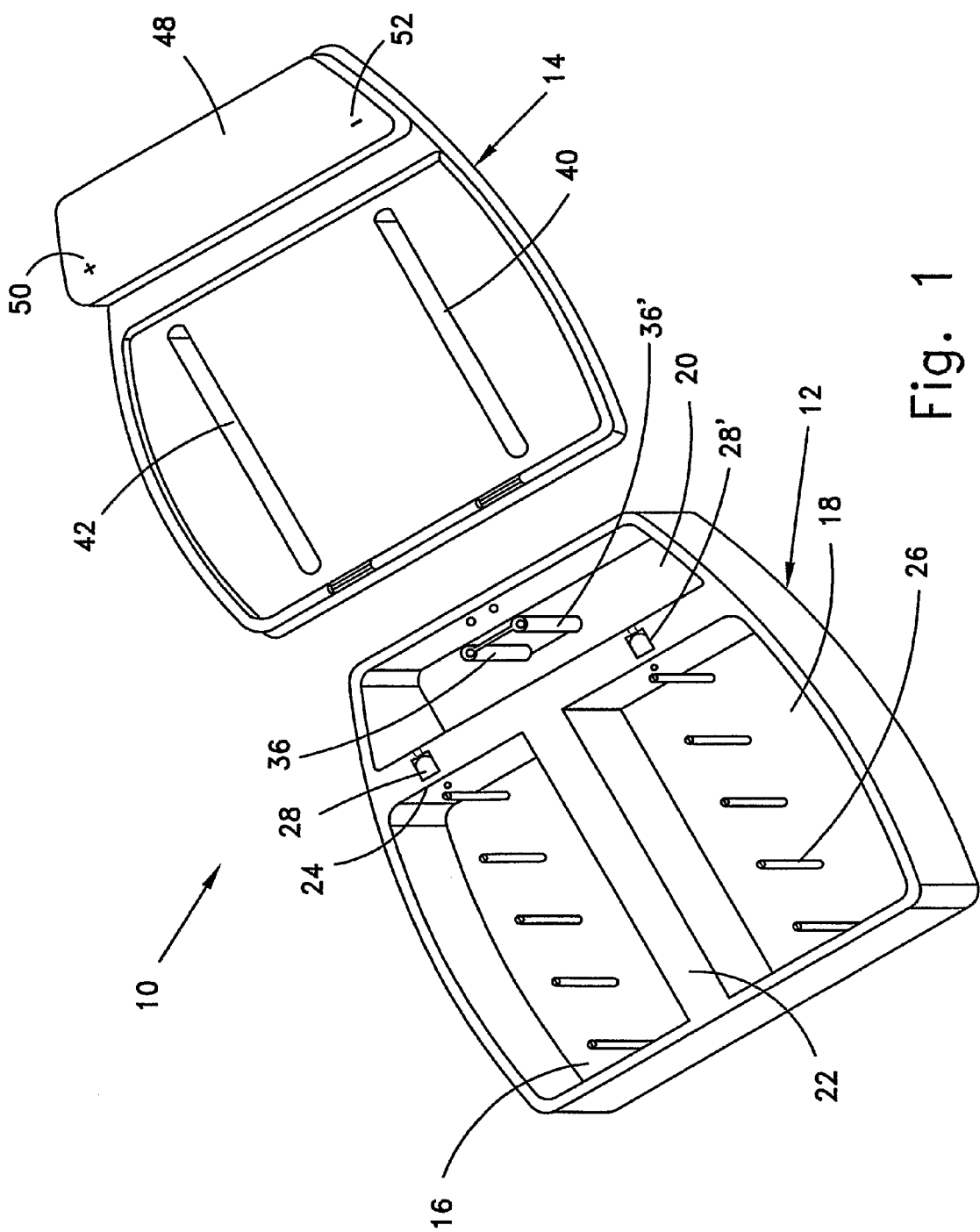
FIG. 1 illustrates an exploded perspective view of the base and cover of the apparatus of the present invention.
Figure 2:
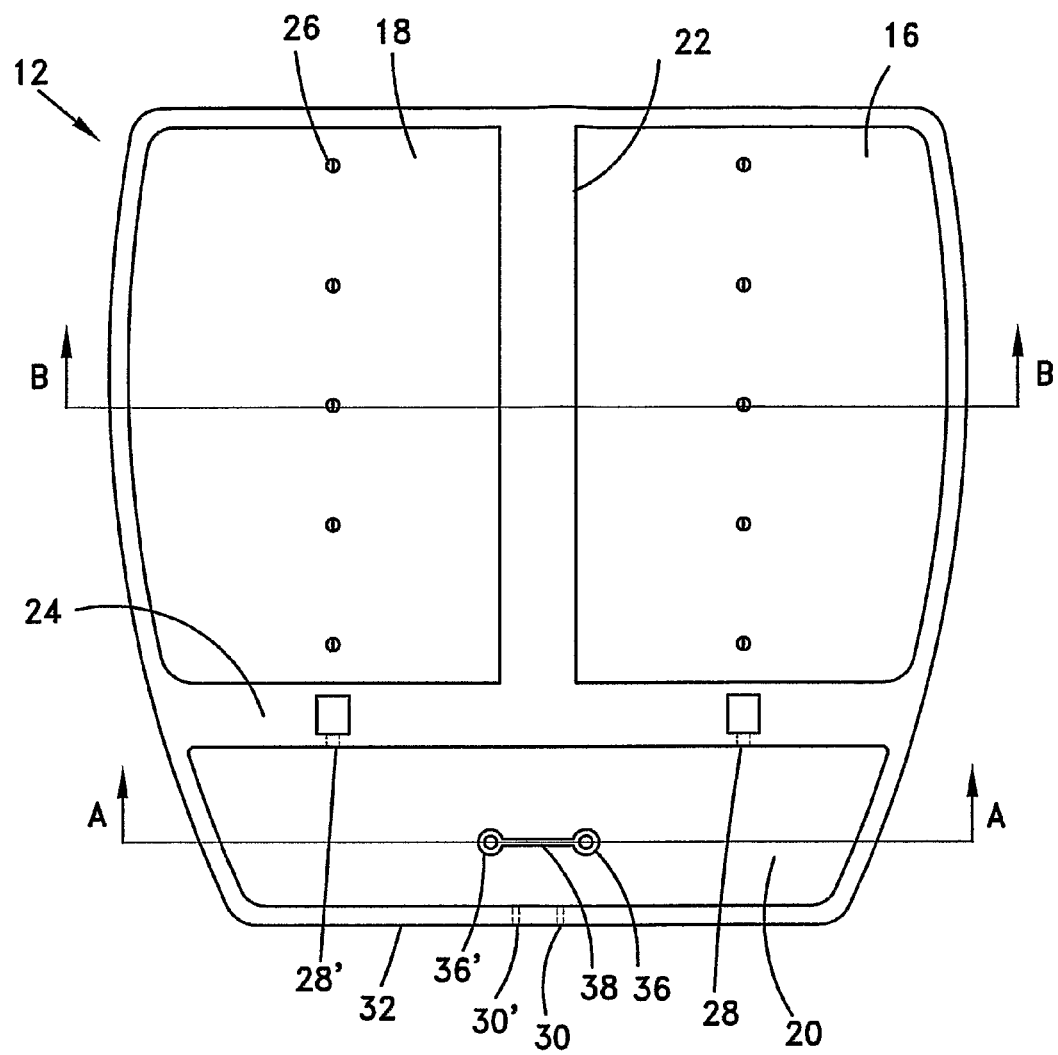
FIG. 2 illustrates a top view of the base of the apparatus of the present invention.
Figure 5:
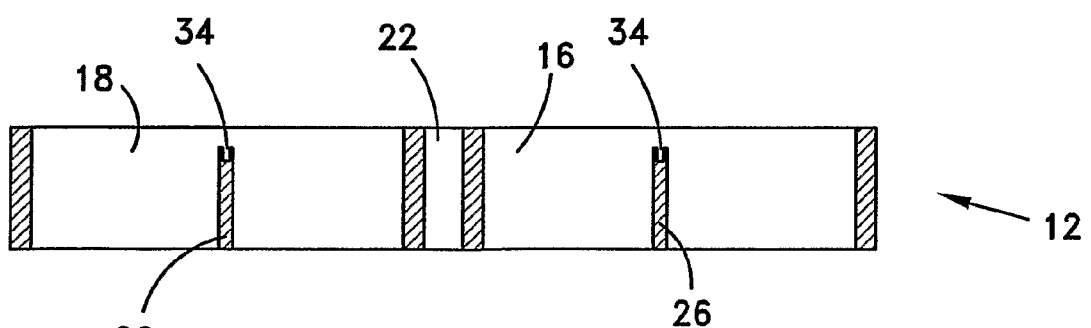
FIG. 5 illustrates a cross-sectional view of the base of the apparatus of the present invention, cut transversely through the partition between the receptacles, and through the pins, along B-B in FIG. 2.

The apparatus (10), as shown in FIG. 1, comprises a base (12) and a cover (14). Referring in particular to FIGS. 1 and 2, the base (12) consists of three compartments, or, receptacles, (16), (18) and (20), wherein two receptacles (16) and (18) are arranged in parallel, and, when enclosed by cover (12), define a double chamber for accommodating an appropriate buffer solution. A partition (22) separates the first receptacle (16) from the second receptacle (18) such that no communication takes place between the two receptacles, thereby forming non-communicating, independent receptacles. Alternatively, partition (22) is not present, and receptacles (16), (18) are simply separated from each other by a space between them (not shown in the figures). Each receptacle (16), (18) contains an array of pins (26) that protrude vertically from the bottom of the respective receptacles (16), (18). The pins (26) are arranged to run longitudinally within the respective receptacles (16), (18), essentially parallel to the partition (22). Each pin (26) extends upward to a distance that is lower than the upper edge of the side walls of each receptacle (16), (18), and preferably at approximately the same height as, or slightly lower than inlets (28), (28'). As can be seen most clearly in FIG. 5, the top of each pin (26) contains a narrow slit (34) that runs parallel to the partition (22). Each slit (34) is wide enough and deep enough for an electrode to run through it, as shall be further described herein below.

The receptacles (16), (18) are substantially identical, and mirror images of each other and may accommodate equal amounts of the buffer solution. The buffer solution preferably fills each respective receptacle (16), (18) such that the tops of the pins (26) as well as the electrode are completely submerged below the buffer.

According to the preferred embodiment, there is no communication, and therefore, no contact between the anode and cathode. A voltage gradient is created only when a bond, for example a conductive gel matrix, joins the two receptacles (16), (18), thereby defining a semi dry electrophoresis system. This design is intended as an operation safety feature for avoiding an electrical hazard, as described herein below.

Figure 3:
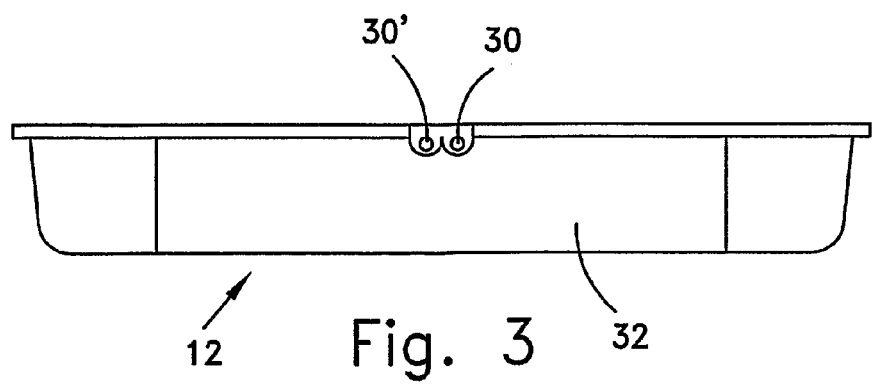
FIG. 3 illustrates a back view of the base of the apparatus of the present invention.

As shown in FIGS. 2 and 3, two openings (30), (30'), through which external electrically conductive wires are inserted, are situated at the back wall (32) of the third compartment (20). When the cover (14) is placed on the base (12), the third compartment (20) remains in communication with the external environment via openings (30) (30'). The openings (30), (30') are located adjacent to one another and approximately in the center of the back wall (32) of the third compartment (20).

Figure 4:
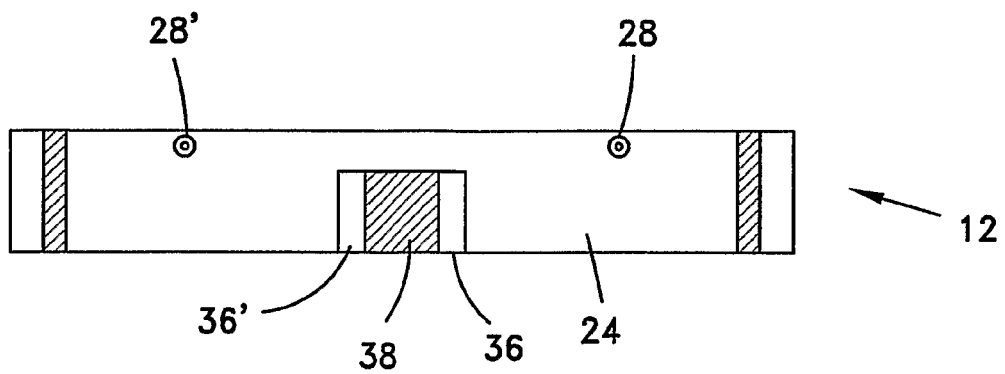
FIG. 4 illustrates a cross-sectional view of the base of the apparatus of the present invention, cut transversely through the two hollow vertical fingers, along A-A in FIG. 2.

FIGS. 1, 2 and 4 show two hollow fingers (36), (36') that protrude vertically from the bottom of approximately the center of the third compartment (20). The fingers (86), (36') are situated in front of the openings (30), (30'), and are joined to each other by a tab (38).

Figure 6A:
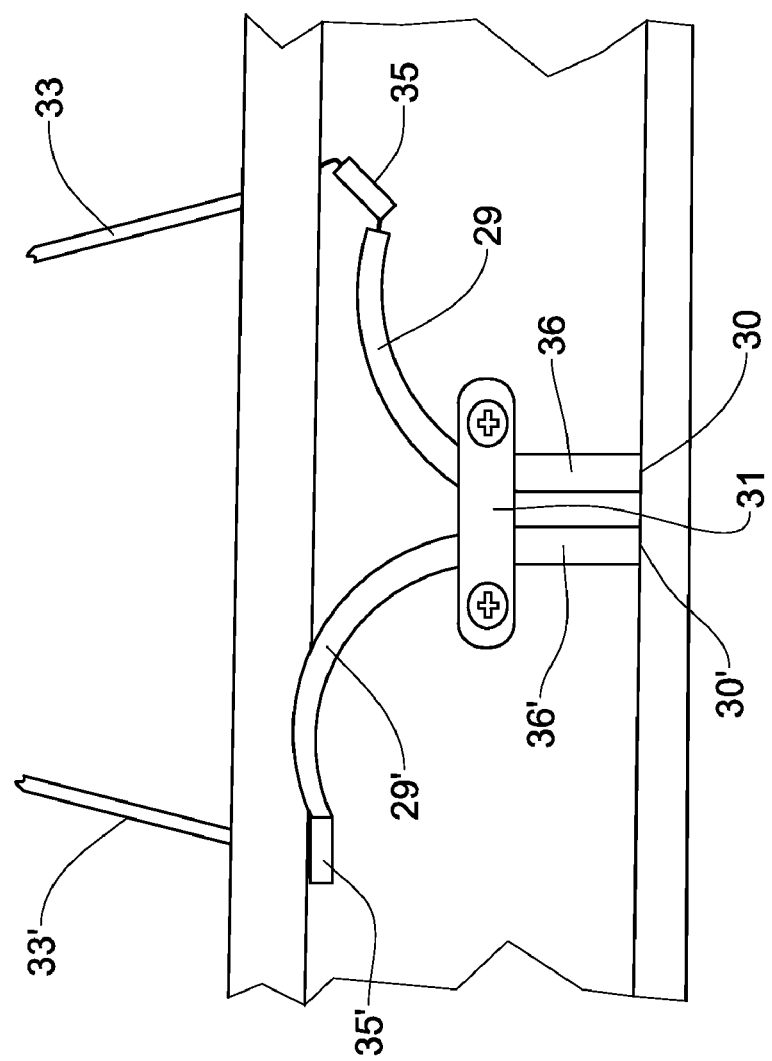
FIG. 6a illustrates a method of securing the external wires and the electrodes within the third compartment.

In a preferred embodiment shown in FIG. 6a, two external electrically conductive wires (29), (29') pass through openings (30), (30') and are fastened in place by a brace (31) that is secured by screws into the hollow fingers (36) (36'). The external wires (29), (29') may be joined to the electrodes (33) by a metal clamp (35), by soldering or any other suitable joining means.

Figure 6B:
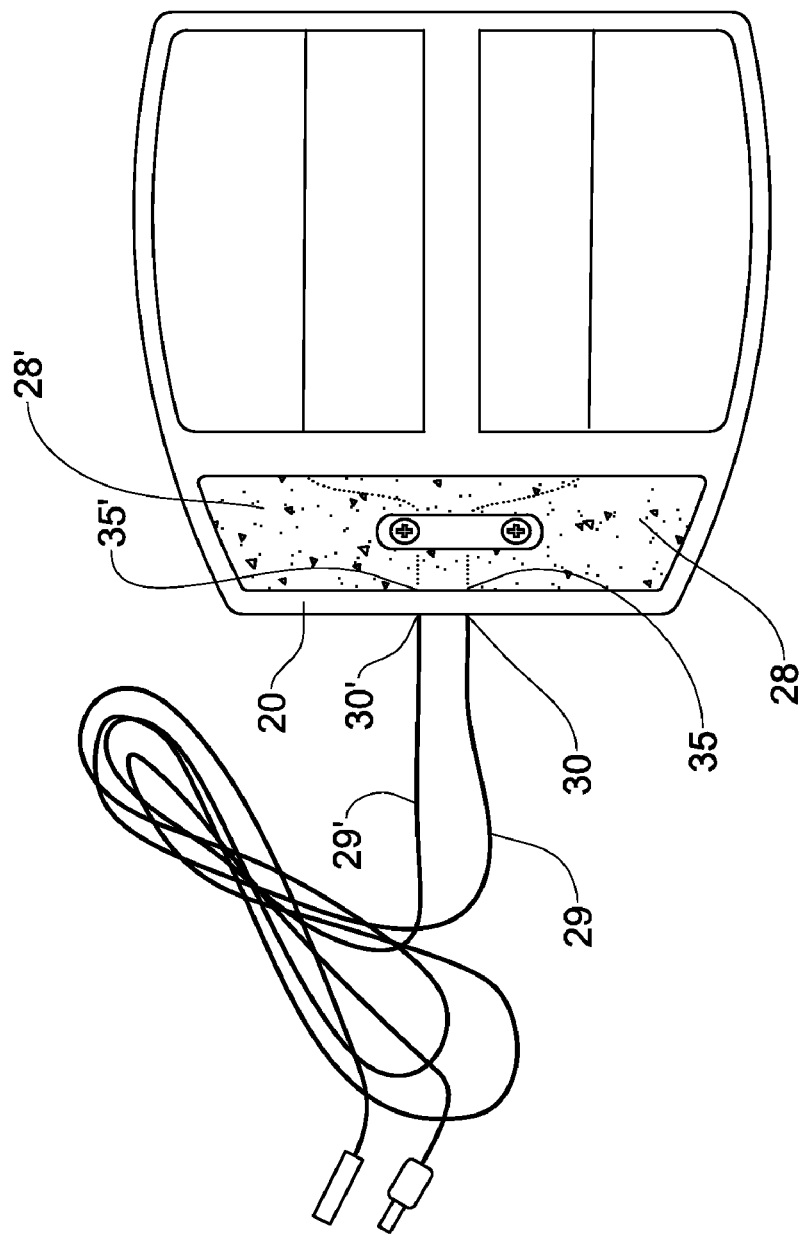
FIG. 6b illustrates the third compartment having an solidified epoxy covering the external wires and electrodes.

As shown in FIG. 6b, the third compartment (20) may be filled with a suitable liquid polymer (e.g. epoxy) which solidifies and completely covers the wires (29), (29') as well as the exposed wire/electrode connection. The epoxy isolates the electrodes (33), thereby preventing contact with any medium that may cause damage thereto.

The electrodes may be clad with platinum or some other relatively inert material to prevent chemical reaction with an electrolyte The third compartment (20) is separated from the receptacles (16), (18) by a transverse wall (24). Still referring to FIGS. 1, 2 and 4, the third compartment (20) is in communication with each buffer receptacle (16), (18) via inlets (28), (28'), which are situated at the wall (24). One inlet ( ) facilitates communication between the third compartment (20) and a first receptacle (16) and the other inlet (28') facilitates communication between the third compartment (20) and the second receptacle (18). The inlets (28), (28) are located at a height on the wall (24) that is slightly above the tips of pins (26), such that an electrode that passes through each of the inlets (28), (28') would rest in the slits of the respective pins (26) located in the respective receptacles (16), (18). The inlets (28) (28') at the ends that open into the receptacles (16) (18) (i.e. the downstream openings) are preferably just large enough for the electrodes to pass through, thereby substantially plugging up the inlets (28), (28'), in order to prevent the buffer from escaping through them. The inlets (28) (28') comprise a hole or slit, and the preferred diameter of the downstream opening is between 0.7 mm and 1.4 mm.

In an alternative embodiment (not shown), the base (12) comprises only first and second receptacles (16), (18). The inlets (28), (28') allow the receptacles (16), (18) to be in communication with the external environment. Electrodes are passed through each inlet (28), (28') and external wires (29), (29') are connected to the electrodes as described above for the first embodiment.

Figure 7:
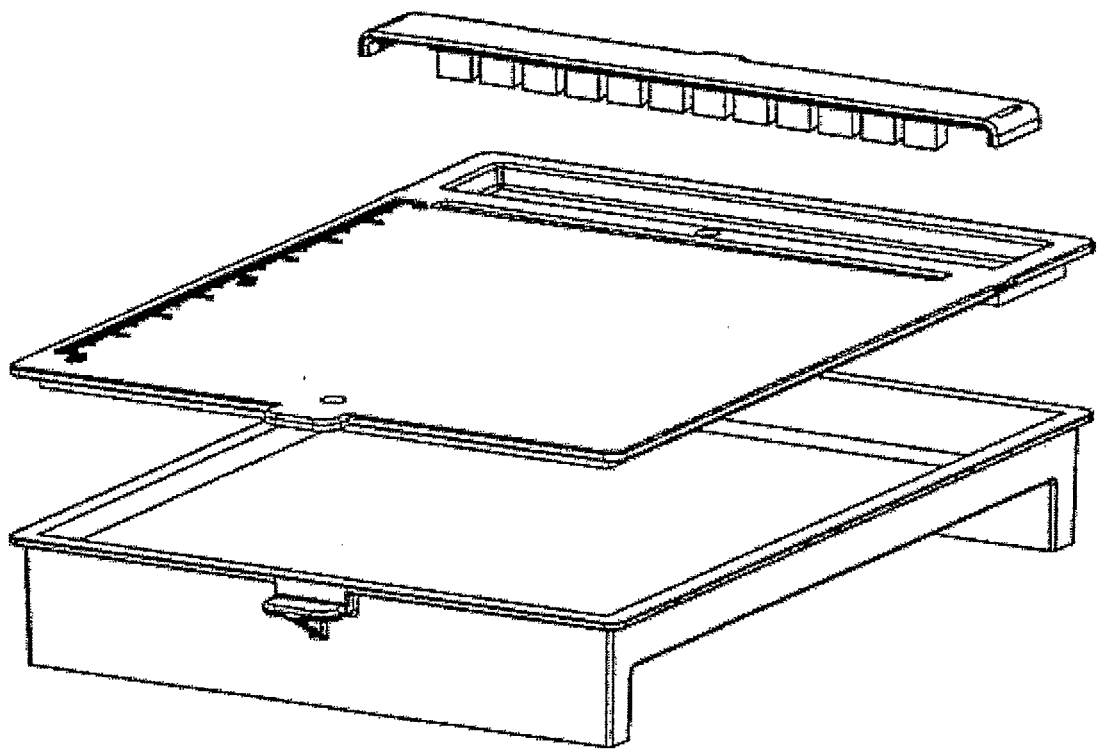
FIG. 7 illustrates the cassette described in WO 02/37904, in an exploded view.

The cover (14) of the apparatus (10) may be constructed such that it covers only the two receptacles (16), (18), or to also cover the third compartment (20), as is shown in the figures herein. The cover (14) is adapted to receive a cassette or tray that contains within it a gel, which is intended for electrophoresis. The cassette (11) described in WO 02/37904, and shown herein in an exploded view in FIG. 7 is particularly suitable for use with the apparatus (10) of the present invention. Referring to FIGS. 1 and 8-12, each of the two elongated narrow slots (40), (42), run longitudinally, significantly close to the respective outer longitudinal edges (60), (62), of the cover (14). Additional slots may be added if required. When cover (14) is situated on top of base (12), each lot (40), (42) is aligned above one of each respective receptacle (16), (18) and is intended to accommodate protruding members of the gel cassette or tray (shown in FIG. 7) such that the electrophoresis gel is in communication with the receptacles (16) (18).

Figure 10:
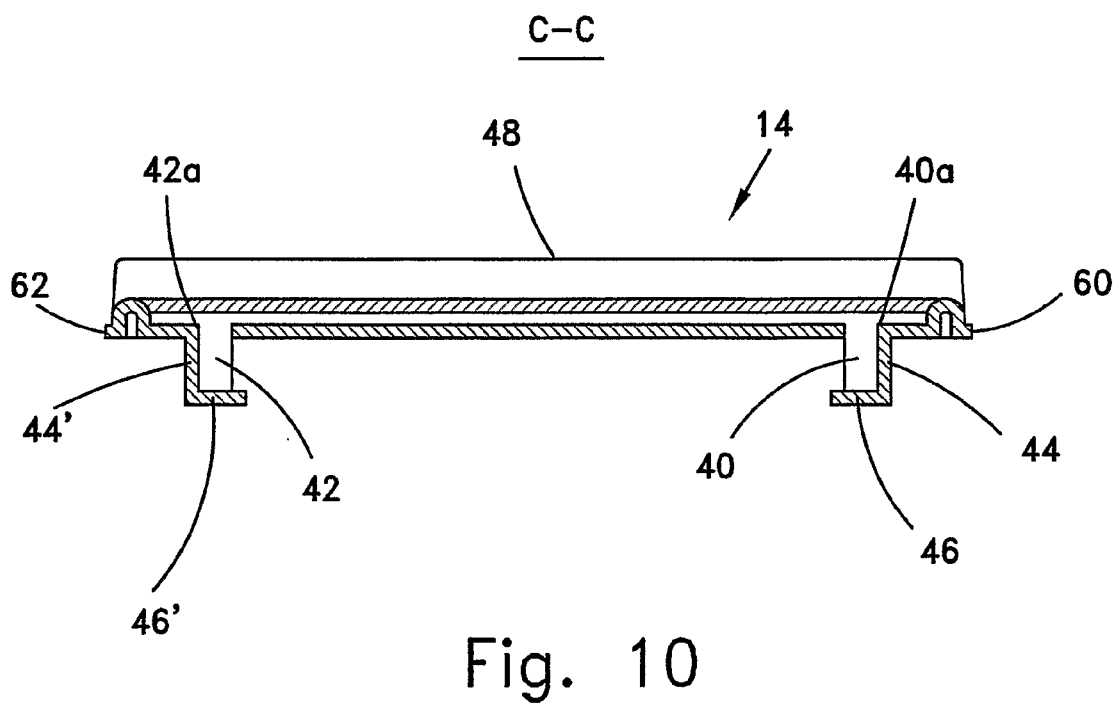
FIG. 10 illustrates a cross-sectional view of the cover of the apparatus of the present invention, cut transversely through the rectangular slots, along C-C in FIG. 7.
Figure 11:
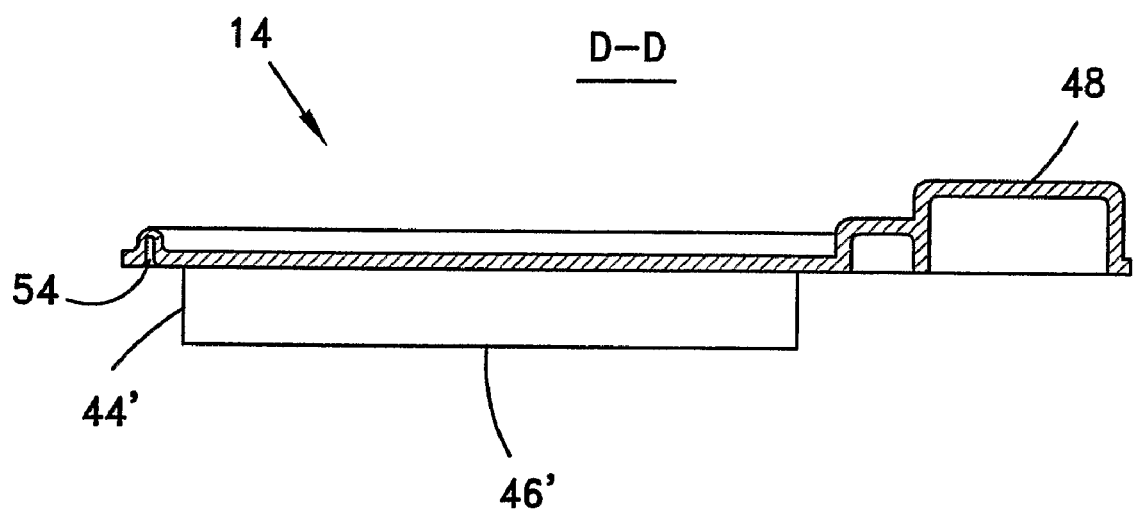
FIG. 11 illustrates a cross-sectional view of the cover of the apparatus of the present invention, cut longitudinally through one of the vents, along D-D in FIG. 7.

Referring in particular to FIG. 10, legs (44), (44') extend downward from the underside of cover (14) at the longitudinal edge (40a), (42a) of each respective slot (40), (42), which is in proximity to the outer longitudinal edge (60), (62) of cover (14), and feet (46), (46') extend outward at the bottom end of legs (44), (44'), orthogonal thereto. The legs (44), (44') and feet (46), (46') serve as a stand when placing the cover (14) down on a surface outside of the base (12). Additionally, the legs (44), (44') and feet (46), (46') prevent external bodies from entering the receptacles (16), (18) when the cassette or tray is not situated thereon, and causing damage to the electrodes, or unintentionally completing the electrical circuit.

During operation of the apparatus, electrolyte gas bubbles are formed. Preferably, all of the bubbles flow along the buffer solution and exit the receptacles (16), (18) through the vents (54), (56) (see FIG. 8), as described herein below. However, if bubbles flow to and contact the gel submerged in the buffer solution, the gas contained within the bubbles will separate the gel from the buffer solution, resulting in a temporary discontinuation of the fluid communication between the gel and the buffer solution. This occurrence will produce flawed data from the electrophoresis process. Hence, in an alternative arrangement, shown in FIG. 10a, each leg (44a), (44a') is situated between each respective slot (40), (42) and the central longitudinal axis (64) of cover (14), and extends orthogonal therefrom. Legs (44a), (44a') serve as a barrier for preventing electrolyte bubbles from reaching the slots (40), (42), and therefore, the gel. Optionally, legs (44a), (44a') extend longitudinally all the way to the vents (54), (56) in order to direct bubbles to the vents (54), (56). Feet are not shown in the figure, and are generally unnecessary, however, they may be present if desired.

The cover (14) reduces the potential buffer evaporation during electrophoresis by maintaining the buffer chambers (16), (18) closed. It also reduces the probability of liquid spills.

The buffer solution may reach temperatures of up to 40° C. in each chamber (16), (18) during electrophoresis. However, the temperature of the area immediately surrounding the partition (22) (see FIG. 1) that separates the receptacles (16), (18) remains cooler than the temperature of the buffer. When cover (14) is situated above the receptacles (16), (18), and the cassette and gel are situated thereon, a temperature gradient is created, which affects the movement of the molecule samples across the gel, and may distort the results by producing uneven band separation. Therefore, according to a preferred arrangement, shown in FIG. 12, the upper surface of cover (14) comprises a heat sink (66) made of a heat conducting material such as aluminum, for uniformly distributing the heat produced in each of the chambers (16), (18) across the length of the gel that is situated in a cassette on the upper surface of cover (14). The heat sink (66) preferably extends transversely across the upper surface of cover (14), between legs (44a), (44a').

A raised portion (48) is situated at the back end of the cover (14) and contains substantially the same profile as that of the third compartment (20) that is located directly below the raised portion (48). Positive (+) (50) and negative (−) (52) notations are marked on opposite transverse ends of the raised portion (48), and correspond to each of the receptacles (16),

(18) respectively. Positive (+) (50) and negative (−) (52) notations are intended to aid the user by indicating the proper orientation for the connection of the external wires to the device.

As described above, the buffer solution that fills the receptacles (16), (18) can reach high temperatures during electrophoresis. Thus, vents (54), (56) are necessary in order to release some of the heat as well as the electrolyte bubbles from the enclosed chambers (16), (18). As seen in FIG. 8, two vents (54), (56) in the form of slits are located at the front end of the cover (14), each one correspondingly above one receptacle. Additionally, surplus buffer may overflow out of the apparatus via the vents (54), (56).

Figure 12:
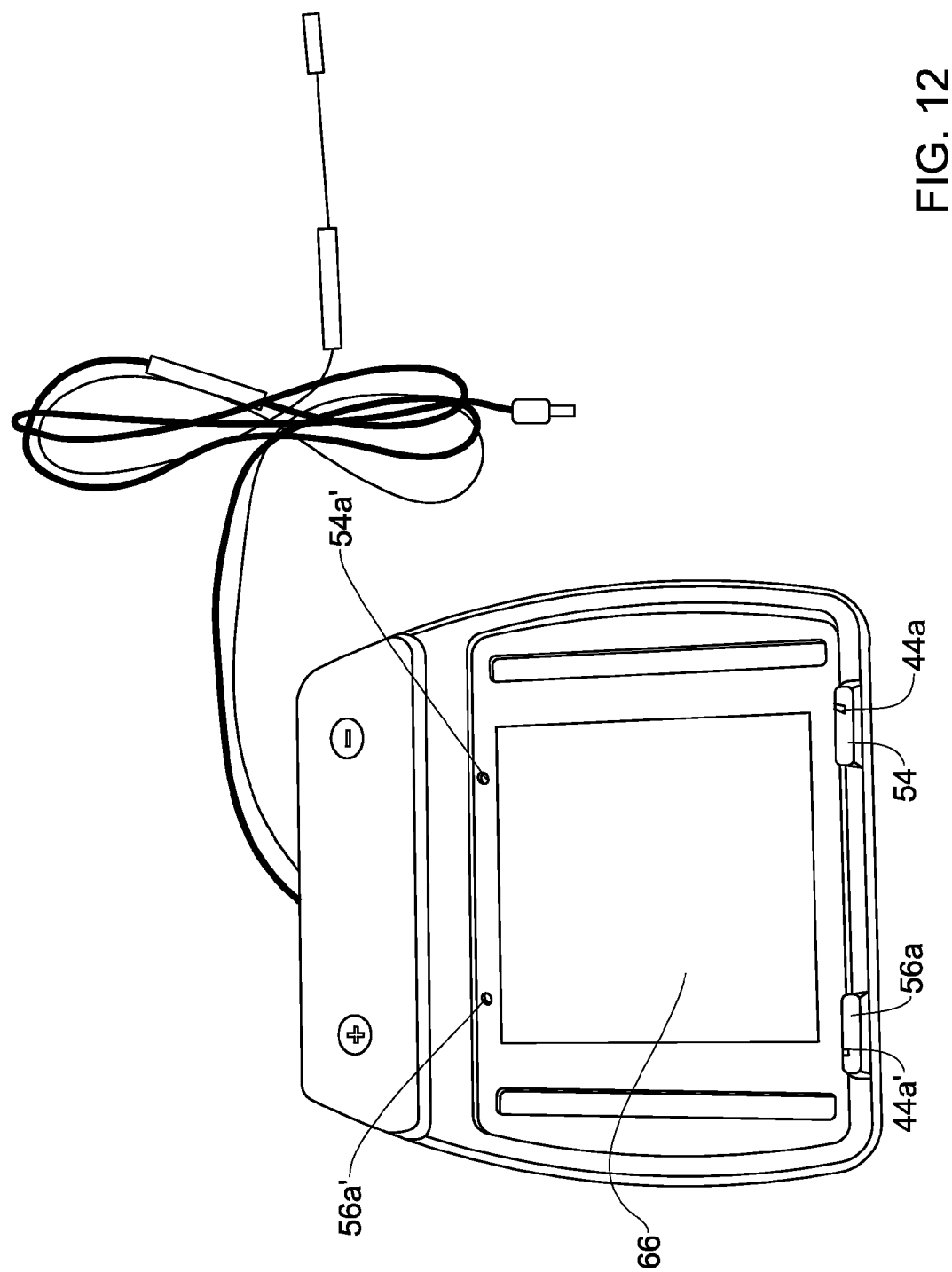
FIG. 12 illustrates a preferred embodiment of the cover of the present invention, comprising a heat sink positioned on its upper surface.

Alternatively, as seen in FIG. 12, vents (54a), (56a) may be openings in the cover, larger than the slits shown in FIG. 8. Additional vents may be added to cover (14), for example, holes (54a'), (56a') situated longitudinally opposite vents (54a), (56a) in FIG. 12.

As described above, when the apparatus (10) is used according to the preferred method, the two receptacles (16), (18) remain separated from each other, and not in electrical communication, even when cover (14) is situated on base (12). Electrical communication is achieved when a conductive object is simultaneously inserted to each receptacle (16), (18) through respective slots (40), (42). Slots (40), (42) are particularly narrow for preventing objects from unintentionally being inserted therethrough and achieving electrical communication between the chambers (16), (18). Nevertheless, additional safety precautions are preferred for preventing undesirable electrical communication between chambers (16), (18). Therefore, in a preferred embodiment of the present invention, electrical communication between chambers (16), (18) cannot be achieved without closing the connection between the contacts of a microswitch.

Figure 13:
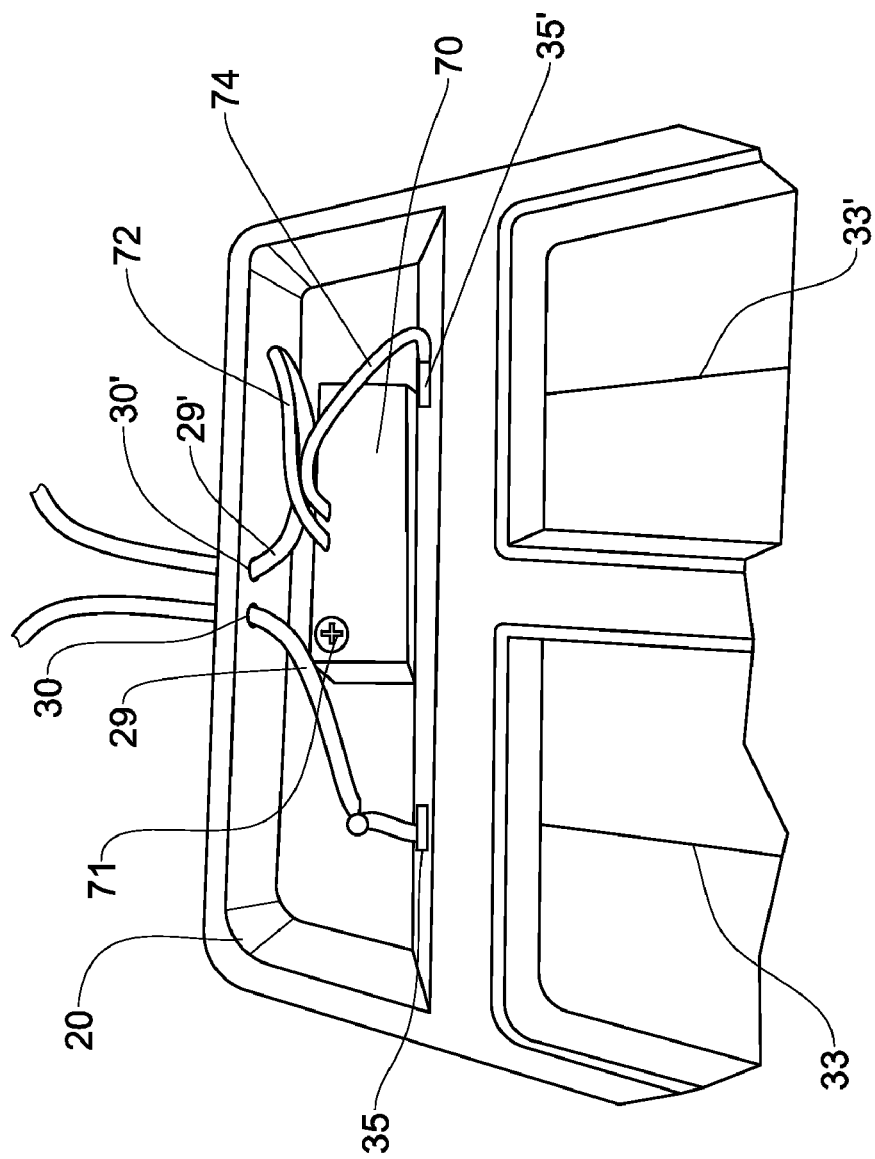
FIG. 13 illustrates a preferred embodiment of the present invention, wherein the third compartment comprises a microswitch.
Figure 14:
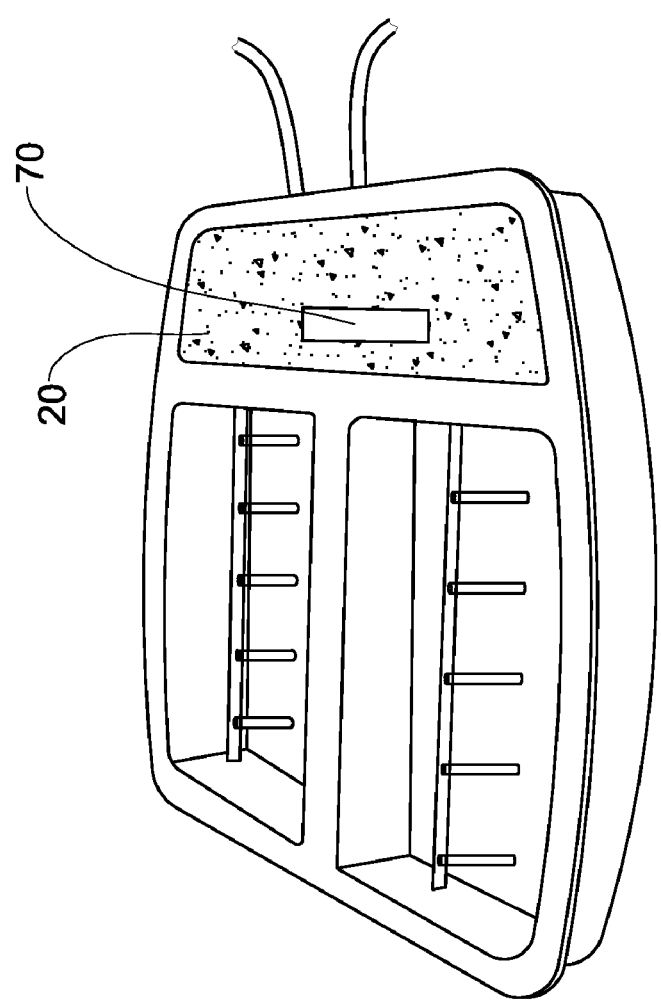
FIG. 14 illustrates the third compartment filled with epoxy, wherein the microswitch is partially exposed.
Figure 15:
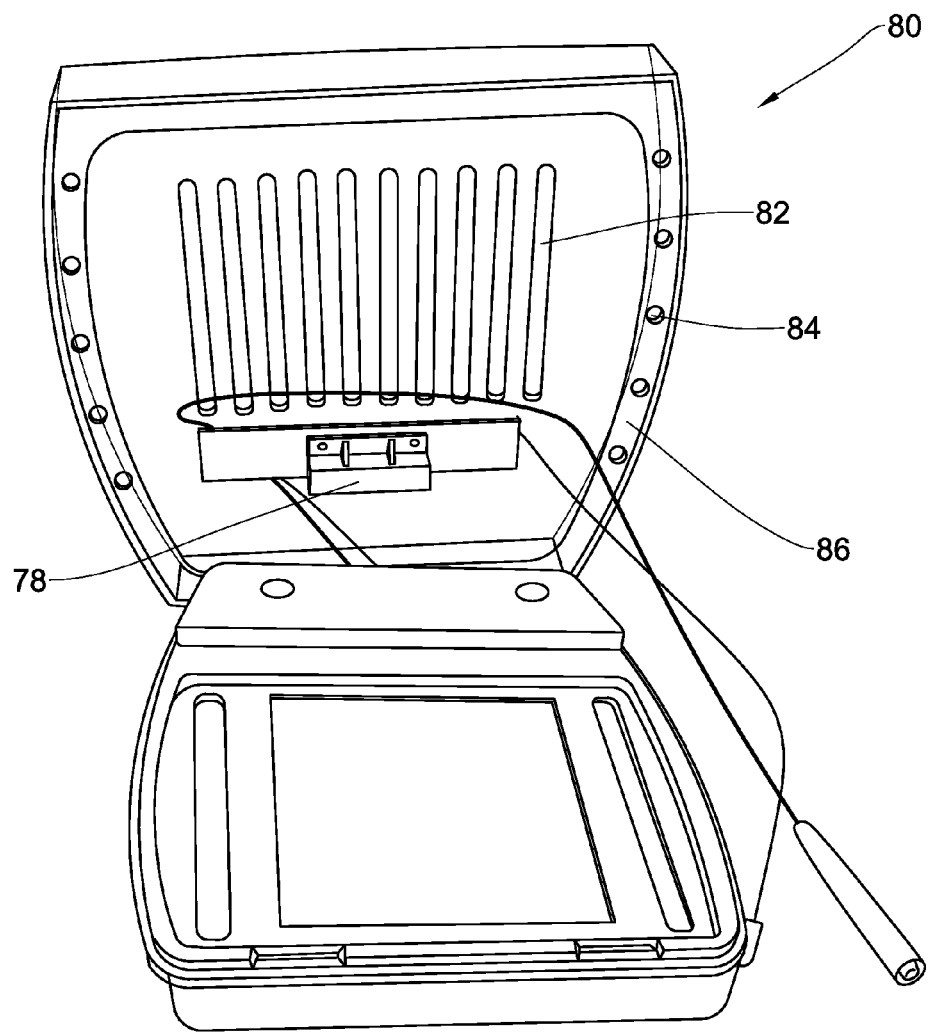
FIG. 15 illustrates the underside of the outer casing having a magnet affixed thereto.

FIG. 13 shows third compartment (20), wherein a microswitch (70) is secured to one of hollow fingers (36), (36') (not seen in the figure) by a screw (71). The two external electrically conductive wires (29), (29') pass through openings (30), (30'). One external wire (29) is joined to electrode (33) by a metal clamp (35). The other external wire (29') is joined to first lead wire (72) of microswitch (70). Second lead wire (74) of microswitch (70) is joined to electrode (33') by metal clamp (35'). Third compartment (20) is filled with liquid epoxy as described herein above. FIG. 14 shows third compartment (20) containing solidified epoxy. External and lead wires are substantially submerged below the epoxy, and the upper surface of microswitch (70) is exposed above the epoxy. An outer casing (80) shown in FIG. 15 comprises a mechanical stimulus, such as a magnet (78) affixed to its underside. When outer casing (80) is positioned on apparatus (10), shown in FIG. 16, magnet (78) is in close proximity to microswitch (70) and the switch is closed, thereby completing the electric circuit. Thus, according to this embodiment, even when the cassette is situated on cover (14) and the gel is in communication with each receptacle (16), (18), electrical communication between receptacles (16), (18) does not take place until outer casing (80) is positioned on apparatus (10).

Outer casing (80) comprises a plurality of vent slots (82) on its upper surface for allowing heat to escape therethrough, and a plurality of vent holes (84) located around its lower rim (86) for allowing cool air to enter therethrough.

Figure 16:
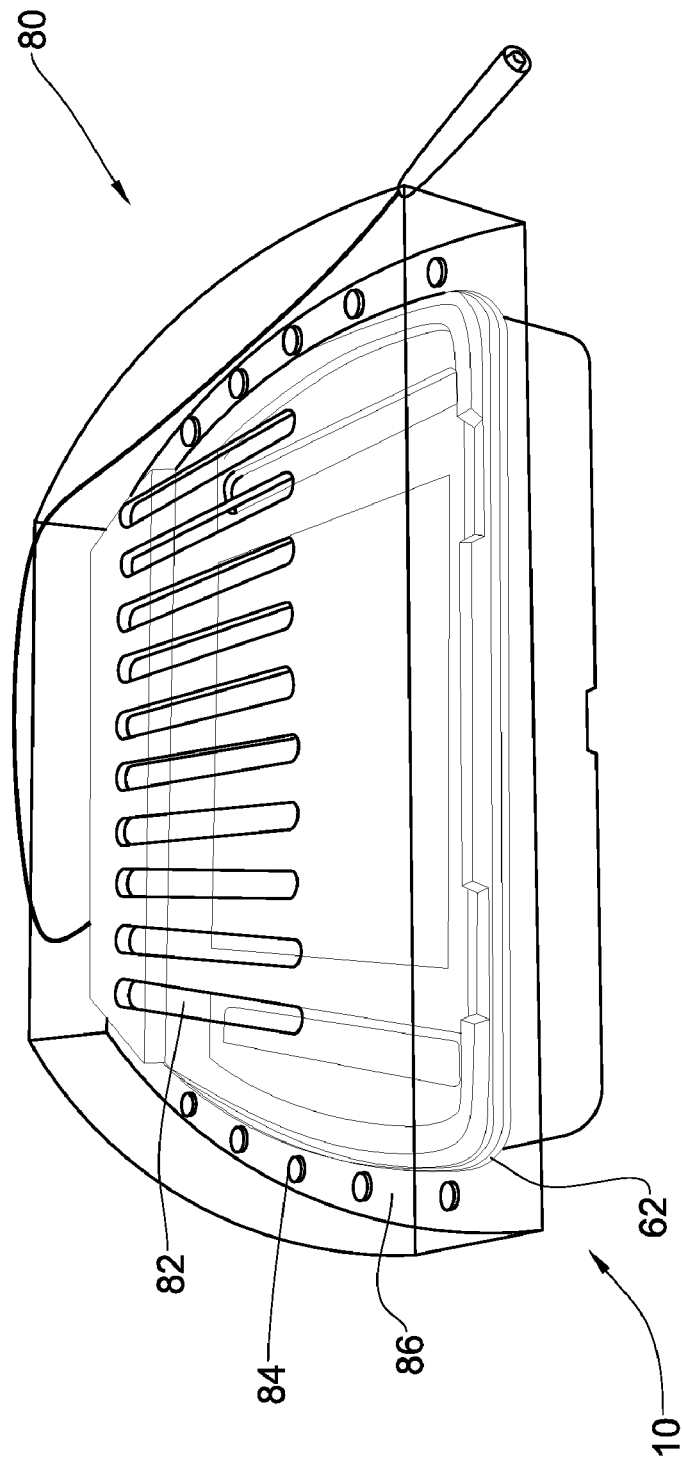
FIG. 16 illustrates the outer casing positioned on the apparatus of the present invention.

Lower rim (86) is shown in FIG. 16 resting an outer edges of cover (14), however outer casing (80) may alternatively fully enclose apparatus (10) (not shown in Figs.)

The device of the invention is preferably small in size, contains a relatively small amount of buffer, is portable and easy to use. The tank includes two electrophoresis receptacles, two platinum electrode panels, a cover, and power leads. The tank consists of a molded electrophoresis receptacle that requires only 75-80 ml of buffer, and may be made of ABS plastic with a specially designed attached lead that prevents accidental electrical exposure.

Platinum electrodes are corrosion resistant, and provide a uniform electrical field. The platinum wire in the electrode panels is protected in recessed channels.

According to a preferred embodiment, the apparatus (10) comprises a dedicated external electrical power supply, which provides low voltage, for example, 12V. The third compartment (20) comprises a transformer for converting to high voltage, for example, 160V.

Uses and Mode of Operation

The present invention is intended to be used for horizontal gel electrophoresis using agarose, polyacrylamide, gradient and hybrid gel matrixes. In addition to the regular separation of nucleic acids and proteins according to their molecular weight, the present invention is useful for additional purposes, such as purification of impurities by separating from large mixtures of compounds into a variety of pure groups.

As used herein, the term "nucleic acid" refers to oligo and polynucleotides such as deoxyribonucleic acid (DNA) and ribonucleic acid (RNA). The terms should also be understood to include, as equivalents, analogues of either RNA or DNA made from nucleotide analogues, and single-stranded or double-stranded polynucleotides.

The term "proteins" refer to one or more chains of amino acids (polypeptides and muiltipolypeptide proteins respectively) and comprise proteins or part of them (domains), oligogopeptides and equivalent molecules having amino acid analogues. The proteins can be conjugated or modified and with different functions, for example: antibodies, cytokines, hormones and enzymes.

The electrophoretic tank of the invention is intended to be used together with an intermediate matrix such as gel device, preferably that described in WO 02/37094.

The intermediate matrix connecting the buffers may be comprised of any substance capable of conducting electricity, for example agarose or polyacrylamide.

The prepared specimen to be analyzed is deposited in the gel device. The sample to be analyzed is kept out of contact with the electrolyte buffer solution. The gel device is then subjected to an electric field. The electrodes, which are immersed in the electrolytic solution, allow a desired voltage gradient to be created and maintained across the porous substrate when a direct current power source is attached to the electrodes. The electrical potential difference created between the two electrodes, allows the components of the specimen to be analyzed to undergo an ionographic migration.

The term, "in communication with" as used herein refers to the ability of the contents (e.g. buffer solution, electrodes, wires, air, etc.) of a chamber, receptacle or compartment to communicate (in particular, ionically or electrically) with the contents (e.g. buffer solution, electrodes, wires, air, etc.) of another chamber, receptacle or compartment, or with the external environment, or an object situated externally, such as a cassette, a gel or wires. Thus, for example, when one receptacle is described as being "in communication with" another receptacle, communication (e.g. electrical or ionic) between the receptacles may take place.

The terms, "independent", "non-communicating", "separated" or "isolated" as used herein (unless relating to the electrophoresis separation of molecules) refer to the inability of the contents (e.g. buffer solution, electrodes, wires, air, etc.) of a chamber, receptacle or compartment to communicate (in particular, ionically or electrically) with the contents (e.g. buffer solution, electrodes, wires, air, etc.) of another chamber, receptacle or compartment, or with the external environment, or an object situated externally, such as a cassette, a gel or wires. Thus, for example, when one receptacle is described as being independent from another receptacle, communication (e.g. electrical or ionic) between the receptacles does not take place.

It is important to note that in the present invention, although the two receptacles (16), (18) are independent, communication between them may take place by providing an object such as a gel that is in mutual communication with the contents of the two receptacles (16), (18).

The terms electrophoresis "cells", "chambers" and "tanks" are used interchangeably to refer to containers in which the electrophoresis running buffer is contained.

The terms "buffer", "buffer solution" and "electrolyte" are used interchangeably herein.

The disclosed device is for moving charged molecules through a matrix by the application of an electrical field of sufficient strength and applied for sufficient amounts of time so as to move the charged molecules through the matrix.

This device is (a) economics since only small amount of buffer solution is needed, (b) easy to handle: it is small in size and the separating matrix (the gel) is not submerged which avoid spills and contaminations, (c) safe: there is no contact between electrodes, and the electric circuit can be created only when adding the intermediate matrix; additionally, since the matrix is not submerged there are no spills of dangerous substances, such as ethidium bromide, (d) a multipurpose electrophoresis tank since it can use different electro-conducting matrixes.

While only one embodiment of the invention has been described by way of illustration, it will be understood that the invention may be carried into practice with many modifications, variations and adaptations, without departing from its spirit or exceeding the scope of the claims.

The invention claimed is:

1. A tank apparatus (10) for performing horizontal electrophoresis to a sample loaded gel contained within a gel cassette, said apparatus (10) comprising:
   a. a base member (12) comprising at least first and second receptacles (16), (18) for being filled with buffer solution, wherein each of said receptacles (16), (18) comprises an associated inlet (28), (28');
   b. a cover member (14) for covering at least said first and second receptacles (16), (18), thereby forming first and second buffer chambers, said cover member (14) comprising at least two openings (40), (42) for enabling a sample loaded gel of a gel cassette to be externally inserted therethrough into contact with buffer solution contained in said receptacles, wherein each of said openings (40), (42) is aligned above one of each of said first and second receptacles (16), (18) when said receptacles (16), (18) are covered by said cover member (14); and,
   c. a pair of electrodes (33), (33'), wherein each of said electrodes (33), (33') enters a receptacle via an associated inlet and is situated in one of each of said first and second receptacles (16), (18), and wherein said electrodes (33), (33') are connectable to an electrical power supply;

wherein said first and second receptacles (16), (18) are separated from each other by one of a space or partition between them, wherein each of said receptacles (16), (18) comprises suitable supports for supporting each of said electrodes (33), (33'); and wherein said supports consist of an array of pins (26) that extend vertically from the bottom of each of said receptacles (16), (18), and wherein the electrodes (33), (33') are mounted substantially near the top of each of said pins (26).

2. The tank apparatus (10) according to claim 1, wherein said apparatus (10) further comprises a third compartment (20).

3. The tank apparatus (10) according to claim 2, wherein each of said receptacles (16), (18) opens into said third compartment (20) via said inlets (28), (28'), and wherein each of said electrodes (33), (33') is inserted from said third compartment (20) into a receptacle (16), (18) through an associated inlet (28), (28').

4. The tank apparatus (10) according to claim 3, wherein said third compartment (20) comprises openings (30), (30') for connecting the electrodes (33), (33') to an electrical power supply.

5. The tank apparatus (10) according to claim 2, wherein said cover member (14) further covers said third compartment (20).

6. The tank apparatus (10) according to claim 2, wherein a microswitch (70) is situated in the third compartment (20).

7. The tank apparatus (10) according to claim 6, further comprising an outer casing (80) with a magnet (78) mounted thereon such that when said apparatus (10) is covered by said outer casing (80), said magnet (78) is in close proximity to said microswitch (70) for actuating said microswitch for operatively completing an electrical circuit.

8. The tank apparatus (10) according to claim 7, wherein said outer casing (80) further comprises vent openings (82) for allowing hot air to exit said casing (80), and cool air to enter said casing (80).

9. The tank apparatus (10) according to claim 1, wherein said at least one overflow comprises at least one aperture further serving as a vent, and contained in said cover member located above each respective receptacle (16), (18).

10. The tank apparatus (10) according to claim 1, wherein said cover member (14) comprises an upper surface comprising a heat sink (66) situated thereon.

11. The tank apparatus according to claim 1, wherein said cover member (14) comprises an underside and a pair of legs (44a), (44a') extending downward therefrom, for preventing gas bubbles produced in buffer solution from reaching the said openings (40), (42).

12. The tank apparatus (10) according to claim 11, wherein said cover member (14) comprises a central longitudinal axis, and wherein each leg is situated between one of each of said openings and said central longitudinal axis.

13. The tank apparatus (10) according to claim 1, wherein said at least one overflow comprises at least one aperture contained in said cover member, said at least one aperture being different from said at least two openings (40), (42), wherein overflow of buffer solution is channeled away from said apparatus via said at least one aperture.

14. The tank apparatus (10) according to claim 13, wherein said cover member (14) has a peripheral, upwardly projecting rim, and wherein said rim has a cutout associated with said at least one aperture to prevent accumulation of buffer solution over said cover member.

15. The tank apparatus (10) according to claim 1 wherein the mounting of the electrodes (33), (33') on said pins (26) is effected by a slit (34) contained on the top of each of said pins (26) for accommodating said electrode (33), (33').

* * * * *